US00PP32336P2

(12) United States Plant Patent
Probst

(10) Patent No.: US PP32,336 P2
(45) Date of Patent: Oct. 13, 2020

(54) ***COREOPSIS* PLANT NAMED 'GOLDILOCKS'**

(50) Latin Name: ***Coreopsis* hybrid**
Varietal Denomination: Goldilocks

(71) Applicant: Darrell R Probst, Hubbardston, MA (US)

(72) Inventor: Darrell R Probst, Hubbardston, MA (US)

( * ) Notice: Subject to any disclaimer, the term of this patent is extended or adjusted under 35 U.S.C. 154(b) by 0 days.

(21) Appl. No.: 16/602,028

(22) Filed: Jul. 23, 2019

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/16
See application file for complete search history.

*Primary Examiner* — Anne Marie Grunberg
(74) *Attorney, Agent, or Firm* — Penny J. Aguirre

(57) ABSTRACT

A new cultivar of hybrid *Coreopsis* named 'Goldilocks' that is characterized by its compact plant habit reaching an average of 38 cm in height and 55 cm in width, its floriferous and long blooming season of nearly sterile inflorescences that do not require deadheading; bloom commences in late June and lasts until frost in Kensington, Conn., its medium sized inflorescences with ray florets that are solid medium yellow in color, its resistance to powdery mildew (*Podosphaera macularis*) and leafspot (*Pseudomonas cichorii*) and its cold hardiness at least to U.S.D.A. Zone 4.

2 Drawing Sheets

Botanical classification: *Coreopsis* hybrid.
Variety denomination: 'Goldilocks'.

CROSS REFERENCE TO A RELATED APPLICATIONS

This application is related to U.S. Plant Patent for plants derived from the same breeding program that are entitled *Coreopsis* Plant Named 'Starbright' (U.S. Plant Pat. No. 27,413) and *Coreopsis* Plant Named 'Lauren' (U.S. Plant Pat. No. 28,592).

BACKGROUND OF THE INVENTION

The present invention relates to a new and distinct cultivar of *Coreopsis* plant, botanically of hybrid origin and known as *Coreopsis* 'Goldilocks' and will be referred to hereinafter by its cultivar name, 'Goldilocks'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardiness to at least U.S.D.A. Zone 4 in a wide range of flower colors and plant forms.

The Inventor made a controlled cross in August of 2015 in New Braintree, Mass. between an unnamed and unpatented proprietary plant from his breeding program as the female parent (ref. No N2 14-12) and pollen that was pooled from a variety of unnamed and unpatented proprietary plants from his breeding program as the male parent. The exact characteristics of the pollen parent are therefore unknown. 'Goldilocks' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Goldilocks' as a unique cultivar of *Coreopsis*.

1. 'Goldilocks' exhibits a compact plant habit reaching an average of 38 cm in height and 55 cm in width.
2. 'Goldilocks' exhibits a floriferous and long blooming season of nearly sterile inflorescences that do not require deadheading; bloom commences in late June and lasts until frost in Kensington, Conn.
3. 'Goldilocks' exhibits medium sized inflorescences with ray florets that are solid medium yellow in color.
4. 'Goldilocks' exhibits resistance to powdery mildew (*Podosphaera macularis*) and leafspot (*Pseudomonas cichorii*).
5. 'Goldilocks' exhibits cold hardiness at least to U.S.D.A. Zone 4.

The female parent of 'Goldilocks' differs from 'Goldilocks' in having flowers that are pink in color and is very fertile and stops flower production once seed has set. 'Goldilocks' can be most closely compared to *Coreopsis* cultivars 'Starbright' and 'Lauren'. Both are similar to 'Goldilocks' in having ray florets that are yellow in color, disease resistance and a longer blooming season that does not require deadheading. 'Starbright' differs from 'Goldilocks' in having ray florets that are paler yellow in color with a maroon center and cold hardiness only to U.S.D.A. Zone 5. 'Lauren' differs from 'Goldilocks' in having ray florets that are lighter yellow in color, a dense and bushy plant habit and cold hardiness only to U.S.D.A. Zone 5.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to website listings by Emerald Coast Growers, Santa Rosa Gardens, Skagit Gardens, James Greenhouses, and The Greenhouse.

BRIEF DESCRIPTION OF THE DRAWINGS

The accompanying colored photographs illustrate the overall appearance and distinct characteristics of the new *Coreopsis*. The photographs were taken of a 4-month-old plant of 'Goldilocks' as grown outdoors in a 1-gallon container in Kensington, Conn.

The photograph in FIG. 1 provides a side view of 'Goldilocks' and shows the plant habit in bloom.

Figure 1:
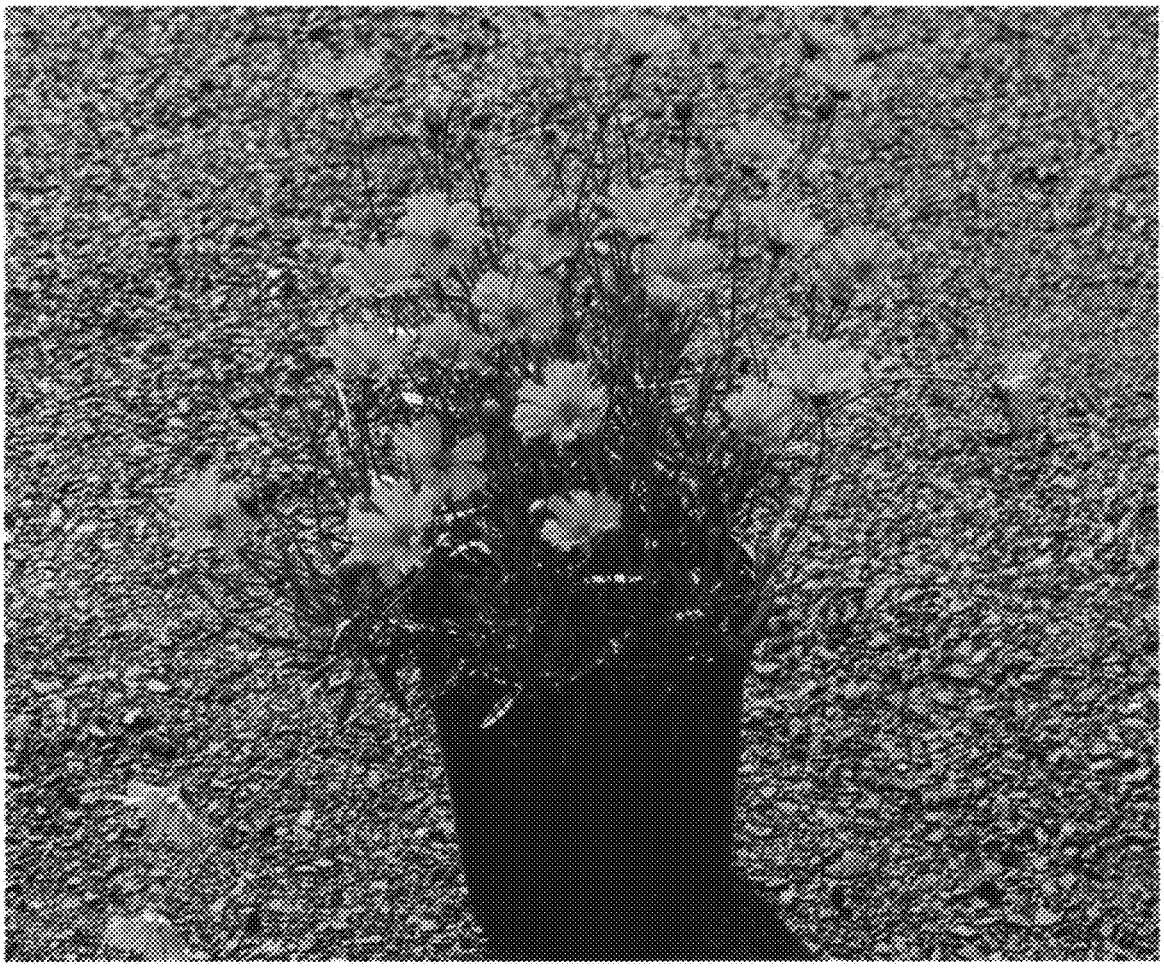
Figure 2:
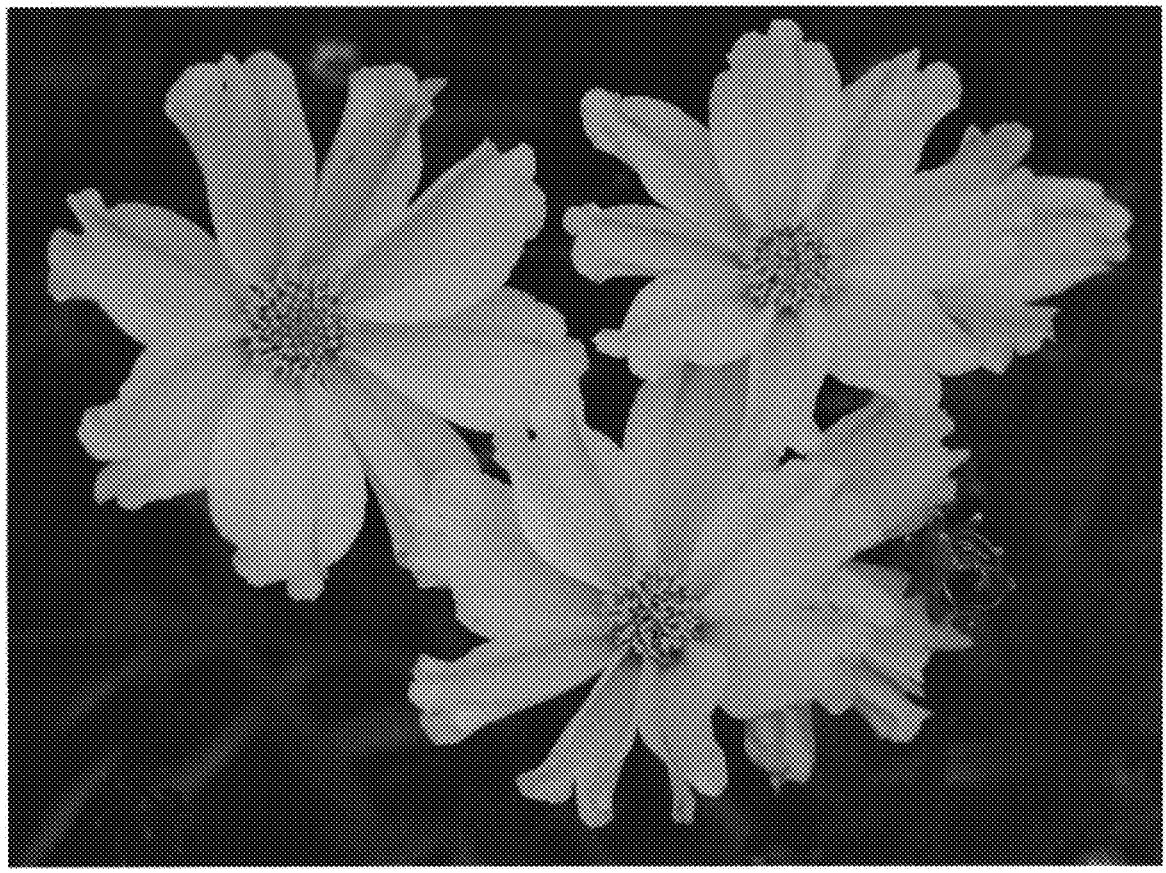

The photograph in FIG. 2 provides a close-up view of the inflorescences of 'Goldilocks'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 4-month-old plants of 'Goldilocks' as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms from late June until frost in Kensington, Conn.

*Plant type.*—Herbaceous perennial.

*Plant habit.*—Clump-forming, compact, upright leafy flowering stems with inflorescences held above the foliage.

*Height and spread.*—Reaching an average of 27 cm in height and 28 cm in width, mature plant reaches 38 cm in height and 55 cm in width as grown in the landscape.

*Cold hardiness.*—At least to U.S.D.A Zone 4.

*Diseases and pests.*—Resistance to powdery mildew (*Podosphaera macularis*) and leafspot (*Pseudomonas cichorii*), no susceptibility or resistance to pests has been observed.

*Root description.*—Fibrous and fine, NN155A in color.

*Propagation.*—Stem cuttings.

*Time required for root initiation.*—An average of 10 days for root initiation.

*Growth rate.*—Vigorous but remiains compact.

Stem description:

*Shape.*—Rounded to tetragonal, solid.

*Stem color.*—144A.

*Stem strength.*—Strong.

*Stem size.*—Main stems; an average of 5 cm in length and 4 mm in width, lateral stems; an average of 10 cm in length (excluding peduncles) and 4 mm in width.

*Stem surface.*—Glabrous, smooth, and dull.

*Branching habit.*—Freely branched, an average of 4 basal main stems, lateral stems typically branched as oppositely arranaged pairs at each node, with an average of 4 lateral stems (2 pairs) per main stem.

*Internode length.*—An average of 5 cm.

Foliage description:

*Leaf division.*—Simple.

*Leaf margins.*—Entire.

*Leaf size.*—Up to 7 cm in length and 1 cm in width.

*Leaf shape.*—Narrow obanceolate.

*Leaf base.*—Cuneate.

*Leaf apex.*—Bluntly acute.

*Leaf venation.*—Pinnate, inconspicuous, same color as leaf.

*Leaf attachment.*—Sessile.

*Leaf arrangement.*—Opposite.

*Leaf surface.*—Upper and lower surfaces; dull and sparsely covered with pubescence.

*Leaf color.*—Young and mature upper and lower surface; 144A.

Flower description:

*Inflorescence type.*—Composite with a single row of ray florets surrounding disk florets in the center, inflorescences are borne on branch terminals in loose corymbs.

*Lastingness of inflorescence.*—8 to 10 days until senescence of ray flowers, phyllarys and disk flowers are persistent.

*Fragrance.*—Very faint pleasant scent.

*Quantity of inflorescences.*—Free flowering, an average of 6 corymbs per main branch, an average of 3 composites per corymb.

*Inflorescence size.*—Corymbs; an average of 17 cm in length and 4 cm in width, composite; an average of 3 cm in depth and 4 cm in diameter with disk portion up to 8 mm in diameter.

*Inflorescence buds.*—Globose in shape, an average of 5 mm in depth and diameter, smooth and shiny surface; color; a blend of 143A and N144A.

*Peduncle.*—Rounded in shape, strong, an average of 13 cm in length and 1 mm in diameter, 144A in color, smooth and glabrous surface.

Phyllaries (involucral bracts):

*Phyllary number.*—2 rows; outer (lower) row 8, inner (upper) row 8.

*Phyllary arrangement.*—Outer (lower) phyllaries; 10% fused, held horizontal to slightly upwards with the apex and mid-section recurved downwards, inner (upper) phyllaries; overlap and surround receptacle with apical portion reflexed (campanulate-like).

*Phyllary size.*—Outer (lower) phyllaries; an average of 7 mm in length and 2 mm in width, inner (upper) phyllaries; an average of 1.2 cm in length and 5 mm in width.

*Phyllary color.*—Upper and lower surfaces, outer (lower) phyllaries; 143A, margins 142B, inner (upper) phyllaries; transluscent, a blend of 144A and 151A.

*Phyllary texture.*—Outer (lower) phyllaries; glabrous and smooth on both surfaces, inner (upper) phyllaries; glabrous and slightly waxy on both surfaces.

*Phyllary apex.*—Acute.

*Phyllary base.*—Truncate.

*Phyllary shape.*—Outer (lower) phyllaries; elliptic to lanceolate, inner (upper) phyllaries; lanceolate.

Ray florets (sterile):

*Number.*—8.

*Shape.*—Oblanceolate, with the appearance of 5 longitudinal sections.

*Size.*—An average of 2.1 cm in length and 1 cm in width.

*Apex.*—Rounded with rounded lobes.

*Base.*—Cuneate.

*Margins.*—Entire on sides with lobed and notched apex.

*Aspect.*—Held mainly horizontal and slightly upwards, perpendicular to peduncle.

*Texture.*—Both surfaces; glabrous, dull, and satiny.

*Color.*—Upper and lower surfaces when opening and when fully open; 7A, base lightly flushed with 14A, fading to a blend of 167A before drop.

Disk florets (male and female):

*Number.*—An average of 120.

*Shape.*—Tubular, corolla is fused, flared and slightly curled at apex.

*Size.*—About 6 mm in length and 0.5 mm in width.

*Color.*—En masse; a blend of 7A and 14A, corolla; (tube) base and mid-section transluscent, 163A, top below flare 159D, flared portion 177A.

*Receptacle.*—An average of 6 mm in diameter and 3 mm in depth, 145A in color.

Reproductive organs:

*Presence.*—Disk flowers only.

*Gynoecium.*—1 Pistil; an average of 5 mm in length, style; very fine and 14A in color, bifid pillose, stigma; 14A in color with recurved branches about 0.5 mm in length, ovary is inferior, oblong in shape, an average of 2 mm in length and 1 mm in width, and 145A in color.

*Androecium.*—4 stamens, fused into tube surrounding style, an average of 3 mm in length and less than 0.5 mm in width, 202A in color, no pollen was present.

*Seed.*—Seed development has been observed to be very minimal; nearly sterile, plants available for data collection did not set seed.

It is claimed:

1. A new and distinct cultivar of *Coreopsis* plant named 'Goldilocks' as herein illustrated and described.

* * * * *